United States Patent
Lee et al.

(10) Patent No.: US 9,938,498 B2
(45) Date of Patent: Apr. 10, 2018

(54) METHOD FOR THE INDUCTION AND EXPANSION OF NATURAL KILLER CELLS DERIVED FROM PERIPHERAL BLOOD MONONUCLEAR CELLS

(71) Applicant: NKMAX Co., Ltd., Seongnam-Si, Gyeonggi-Do (KR)

(72) Inventors: Kyung Mi Lee, Seoul (KR); Seon Ah Lim, Seoul (KR); Cassian Yee, Seoul (KR)

(73) Assignee: NKMAX Co., Ltd. (KR)

( * ) Notice: Subject to any disclaimer, the term of this patent is extended or adjusted under 35 U.S.C. 154(b) by 49 days.

(21) Appl. No.: 14/399,371

(22) PCT Filed: May 7, 2013

(86) PCT No.: PCT/KR2013/003981
§ 371 (c)(1),
(2) Date: Nov. 6, 2014

(87) PCT Pub. No.: WO2013/168978
PCT Pub. Date: Nov. 14, 2013

(65) Prior Publication Data
US 2015/0152387 A1 Jun. 4, 2015

(30) Foreign Application Priority Data

May 7, 2012 (KR) .................. 10-2012-0048165
May 7, 2013 (KR) .................. 10-2013-0051442

(51) Int. Cl.
C12N 5/0783 (2010.01)
A61K 35/17 (2015.01)
A61K 39/00 (2006.01)

(52) U.S. Cl.
CPC ............ *C12N 5/0646* (2013.01); *A61K 35/17* (2013.01); *A61K 2039/5158* (2013.01); *C12N 2501/2302* (2013.01); *C12N 2502/1114* (2013.01); *C12N 2502/30* (2013.01)

(58) Field of Classification Search
CPC ............................. C12N 5/0646; A61K 35/17
See application file for complete search history.

(56) References Cited

U.S. PATENT DOCUMENTS

2004/0173778 A1* 9/2004 Roncarolo ........... C12N 5/0636
 252/387
2008/0166326 A1 7/2008 Lowdell
2011/0135687 A1 6/2011 Koelle et al.

FOREIGN PATENT DOCUMENTS

KR 1020120016427 5/2012
WO 2006050270 A2 5/2006
WO 2008118369 A2 10/2008

OTHER PUBLICATIONS

Lee et al, machine translation of KR 10-2012-0016427, published Feb. 24, 2012, pp. 1-32.*
Joao F. Lacerda et al., "Humas Epstein-Barr Virus (EBV)-specific Cytotoxic T Lymphocytes Home Preferentially to and Induce Selective Regressions of Autologous EBV-induced B Cell Lymphoproliferations in Xenografted C.B-17 Scid/Scid Mice", J. Exp. Med, 183:1215-1228, (1996).
Motohashi, S. et al., "A Phase I Study of in vitro Expanded Natural Killer T Cells in Patients with Advanced and Recurrent Non-Small Cell Lung Cancer," *Clinical Cancer Research*, Oct. 15, 2006, 6079-6086, vol. 12, Issue 20, American Association for Cancer Research.
International Search Report dated Jul. 29, 2013 for International Patent Application No. PCT/KR2013/003981 in 5 pages.
Written Opinion dated Jul. 29, 2013 for International Patent Application No. PCT/KR2013/003981 in 6 pages.
Allan et al., "The role of 2 FOXP3 isoforms in the generation of human CD4+ Tregs", *J. Clin. Invest.* 115:3276-3284 (2005).
Numbenjapon et al., "Antigen-independent and antigen-dependent methods to numerically expand CD19-specific $CD8^+T$ cells". Experimental Hematology 35 (2007) 1083-1090.
Tai et al., "CD28 costimulation of developing thymocytes induces Foxp3 expression and regulatory T cell differentiation independently of interleukin 2" *Nature Immunology*, vol. 6, No. 2, pp. 152-162 (2005).
Turtle et al., "Artificial antigen presenting cells for use in adoptive immunotherapy", NIH Public Access, Author Manuscript, *Cancer J.* Author manuscript; available in PMC Jul. 1, 2011 Published in final edited form as: *Cancer J.* 2010 ; 16(4): 374-381.

* cited by examiner

*Primary Examiner* — Laura Schuberg
(74) *Attorney, Agent, or Firm* — Knobbe, Martens, Olson & Bear LLP (57) ABSTRACT

The present invention relates to a method for inducing and expanding natural killer cells derived from peripheral blood mononuclear cells, which comprises co-culturing, as feeder cells, irradiated Jurkat cells and irradiated Epstein-Barr virus transformed lymphocyte continuous line (EBV-LCL) cells in the presence of cytokines, along with peripheral blood mononuclear cells. According to the present invention, a large quantity of natural killer cells can be induced and proliferated from a small quantity of peripheral blood mononuclear cells even without the use of high-cost equipment or various kinds of expensive cytokines, thereby making it possible to significantly improve the efficiency and efficacy of the prevention and treatment of cancer using the natural killer cells.

5 Claims, 6 Drawing Sheets

METHOD FOR THE INDUCTION AND EXPANSION OF NATURAL KILLER CELLS DERIVED FROM PERIPHERAL BLOOD MONONUCLEAR CELLS

CROSS-REFERENCE TO RELATED APPLICATIONS

This application is a national stage application, filed under 35 U.S.C. § 371, of International Application No. PCT/KR2013/003981, filed on May 7, 2013, which claims the benefit of, and priority to, Korean Patent Application Nos. 10-2012-0048165, filed on May 7, 2012 and 10-2013-0051442, filed on May 7, 2013. The contents of each application are incorporated by reference in their entirety.

TECHNICAL FIELD

The present invention relates to a method for inducing and expanding natural killer cells derived from peripheral blood mononuclear cells.

BACKGROUND ART

Immune responses protect a human body from pathogens, and the immune system is composed of many immune-related cells and cytokines. Leukocytes, especially lymphocytes, play an important role in the immune system. Representative examples of cells constituting the lymphocytes include innate immune system cells and acquired immune system cells. Natural killer cells (NK cells) are one of the representative innate immune cells, and known as cells that can kill cancer in a non-specific manner, recognize and kill viruses, bacteria, and the like, and kill pathogens with enzymes such as perforins and granzymes or by Fas-FasL interaction. In the case of cancer patients, a decrease in the ability of such NK cells to kill cancer cells is reported to be deeply associated with the onset of diseases such as lung cancer (Carrega P, et al., Cancer, 2008: 112: 863-875), liver cancer (Jinushi M, et al., J Hepatol., 2005: 43; 1013-1020), breast cancer (Bauernhofer T, et al., Eur J Immunol., 2003: 33: 119-124), uterine cancer (Mocchegiani E., et al., Br j Cancer., 1999: 79: 244-250), blood cancer (Tajima F., et al, Lekemia 1996: 10: 478-482), and the like. Therefore, an increase in the ability and activity of the natural killer cells in regards to killing the cancer cells in cancer patients is essential for cancer treatment. Attempts to treat solid cancer or blood cancer are being currently conducted using such an ability of the NK cells to kill the cancer cells.

To obtain an effect of killing cancer cells, a large quantity of NK cells are needed, but it is difficult to ensure obtaining a large amount of blood from cancer patients, and the NK cells in the blood merely amount to a proportion of approximately 5 to 20%. Thus, since it is difficult to use the NK cells as an immunotherapeutic agent, it is important to extend and proliferate the NK cells effectively. A conventional method of expanding the NK cells typically includes separating or inducing NK cells from bone marrow or mononuclear cells in the blood using an apparatus such as a magnetic activated cell sorter (MACS), cliniMACS, or a fluorescence activated cell sorter (FACS). In such methods, the following operations proceed as follows: 1) separating NK cells from mononuclear cells at early stages and expansion-culturing the NK cells using cytokines; 2) removing T cells coexisting with the mononuclear cells and expansion-culturing the NK cells using cytokines; and 3) inducing the NK cells from stem cells present in the bone marrow. In addition, as the method of isolating NK cells from peripheral blood mononuclear cells (PBMCs) using feeder cells, a method using a RPMI8866 cell line that is derived from B cell leukemia by the Torelli research team from the Republic of Italy, and a method using a HFWT cell line that is derived from a Wilms tumor cell by the Ishikawa research team from Japan have been reported.

However, methods for expanding NK cells reported in the related art are encumbered by the requirement for sophisticated equipment to select cells pre-expansion, the use of genetically engineered feeder cells, and a cocktail of costly cytokines in high concentrations, and thus may be prohibitively expensive for general use, are more difficult to implement and limit accessibility of this approach to the patient population.

DISCLOSURE

Technical Problem

The present invention is directed to providing a novel method for inducing and expanding NK cells derived from peripheral blood, thereby leading to efficient strategy for obtaining activated NK cells derived from peripheral blood without the use of expensive equipment, costly resources or regulatory constraints.

Technical Solution

To solve these problems, one aspect of the present invention provides a method for selectively inducing and expanding NK cells derived from peripheral blood mononuclear cells, which comprises a simplified approach of co-culturing irradiated Jurkat cells and irradiated EBV-LCL cells as feeder cells with the peripheral blood mononuclear cells in the presence of cytokines in defined proportions and concentrations.

Unless specifically stated otherwise, all the technical and scientific terms used in this specification have the same meanings as generally understood by those skilled in the related art to which the present invention belongs. In general, the nomenclature used in this specification and the experimental methods described below are widely known and generally used in the related art.

The present inventors have conducted research to obtain a large quantity of NK cells from a small quantity of blood, and found that the proliferated NK cells can be obtained when mononuclear cells separated from peripheral blood are cultured using irradiated Jurkat cells as feeder cells (Korean Patent Application No. 10-2010-007877).

Figure 1A:
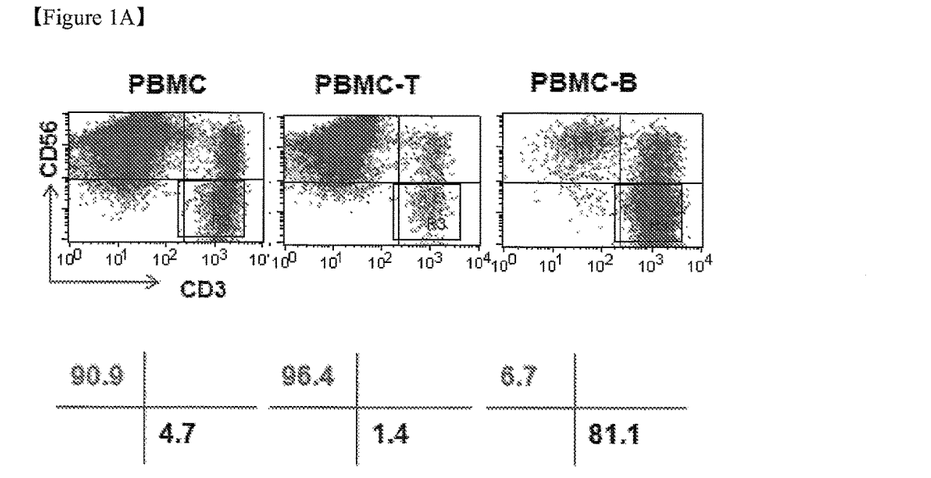
FIG. 1A shows the results obtained by determining levels of inducement into NK cells after mononuclear cells separated from peripheral blood are co-cultured with Jurkat cell lines (PBMC), PBMCs from which only T cells are removed are co-cultured with the Jurkat cell line (PBMC-T), or PBMCs from which only B cells are removed are co-cultured with the Jurkat cell line (PBMC-B).
Figure 1B:
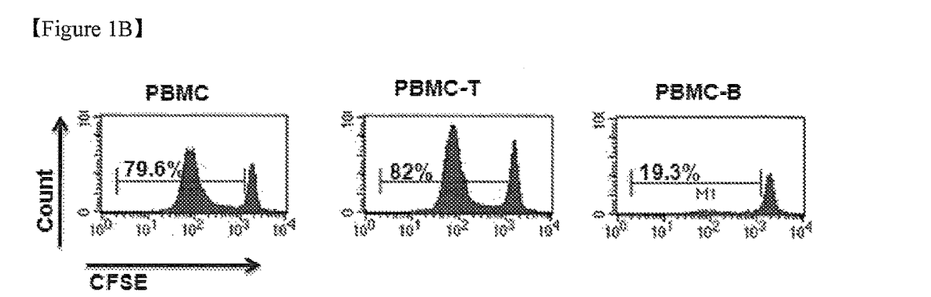
FIG. 1B shows that the NK cells do not selectively proliferate when the PBMCs are co-cultured with the Jurkat cell line to proliferate the NK cells, and B cells are not present within the mononuclear cells.

Also, the present inventors have conducted research on a mechanism in which the NK cells are selectively proliferated using the method disclosed in the patent application, and found that selective proliferation of the NK cells decreases significantly when B cells are removed from mononuclear cells and the mononuclear cells are co-cultured with the irradiated Jurkat cells, indicating that the B cells play an important role in the proliferation of the NK cells (FIGS. 1A and 1B).

Based on these results, it was found that the selective proliferation of the NK cells using the Jurkat cells is dependent on the B cells. From these facts, it was expected that a larger amount of the NK cells can be proliferated when B cell-derived immortalized cells, EBV-LCL, are used as the feeder cells. However, it can be seen that, when the mononuclear cells separated from the peripheral blood are co-cultured with EBV-LCL, the NK cells proliferate, but the purity of the NK cells is significantly lowered. Accordingly, the present inventors have found that all the problems caused when the Jurkat cells or EBV-LCL cells are used alone can be solved when the irradiated EBV-LCL cells are used with the irradiated Jurkat cells as the feeder cells, and the mononuclear cells and NK cells can be proliferated with a much higher yield. Therefore, the present invention has been developed based on these facts.

Therefore, according to one aspect of the present invention, a method for inducing and expanding natural killer cells derived from peripheral blood mononuclear cells is provided, which comprises co-culturing irradiated Jurkat cells and irradiated EBV-LCL cells as feeder cells with peripheral blood mononuclear cells in the presence of cytokines.

In the present invention, the "peripheral blood mononuclear cells," "PBMCs" or "mononuclear cells" refer to mononuclear cells separated from peripheral blood typically used for anti-cancer immunotherapy. The peripheral blood mononuclear cells can be obtained from human blood collected using known methods such as the Ficoll-Hypaque density gradient method.

According to one exemplary embodiment of the present invention, "peripheral blood mononuclear cells" may be obtained from a normal person, a patient at risk of cancer, or a cancer patient. The peripheral blood mononuclear cells used herein do not need to necessarily be autologous, and allogenic peripheral blood mononuclear cells may also be used to induce and proliferate the NK cells for anti-cancer immunotherapy according to the present invention.

When the peripheral blood mononuclear cells are co-cultured with the irradiated Jurkat cells and the irradiated EBV-LCL cells according to one exemplary embodiment of the present invention, the proliferated mononuclear cells and the proliferated natural killer cells may be obtained. A normal person, a patient at risk of cancer, or a cancer patient may be treated with the NK cells thus obtained for prevention and treatment of cancer.

In the present invention, the term "Jurkat cells" or "Jurkat cell line" refers to a blood cancer (immortalized acute T cell leukemia) cell line which has been developed by Dr. Arthur Weiss of the University of California at San Francisco. As cells in which various chemokine receptors are expressed and IL-2 can be produced from the cells, the Jurkat cell line was considered to be a cell line which had no probability as a candidate for the feeder cells (feeder cells) used in anti-cancer immunotherapy since a natural killer cell activation inhibitor, MHC class I, is highly expressed on the cell surface thereof. However, the present inventors have found that many blood cancer cell lines are screened for differentiation of the NK cells from the peripheral blood mononuclear cells and proliferation of the NK cells, and the Jurkat cells are able to be used as the feeder cells (see Korean Patent Application No. 10-2010-0078777). The Jurkat cells used herein may be obtained from the American Type Culture Collection (ATCC; ATCC TIB-152).

In the present invention, the term "EBV-LCL cells" or "EBV-LCL cell line" refers to an Epstein-Barr virus transformed lymphocyte continuous line (EBV-LCL) (D. M. Koelle et al., 1993, supra,). The EBV-LCL cells are often used for research on carcinogenesis, but are not used as the feeder cells to proliferate mononuclear cells and NK cells from the peripheral blood. The EBV-LCL cells according to one exemplary embodiment of the present invention may be directly prepared and used in a typical laboratory. According to one exemplary embodiment of the present invention, the EBV-LCL cells are directly prepared and used. EBV-LCL is a B cell line prepared by transfecting human B cells with an Epstein-Barr virus in vitro. Cyclosporine A is added to suppress T cells reacting to EBV during a procedure of preparing a cell line by transfecting PBMCs with EBV. Specifically, $30 \times 10^6$ PBMCs are added to 9 ml of a culture medium, and the culture medium is placed into a T 25 culture flask. Next, 9 ml of an EBV supernatant is put into the T 25 culture flask. 80 μl of cyclosporine A is then added, and the contents of the flask are cultured at 37° C. After 7 days of culturing, a half of the supernatant is removed, and a fresh culture medium is added. After this, 40 μl of cyclosporine A is added. This procedure is repeatedly performed in the same manner as performed once every 7 days until day 28 of the culture. The cell line may be used after 28 days of the culture. From day 28 on, the cell line is cultured in the culture medium without adding cyclosporine A to the culture medium.

The Jurkat cells and the EBV-LCL cells may be used as the feeder cells even when the Jurkat cells and the EBV-LCL cells are irradiated with radiation to suppress proliferation of cancer cells. According to one exemplary embodiment of the present invention, each of the irradiated Jurkat cells and the irradiated EBV-LCL cells may be obtained by irradiation with radiation of 100 to 500 Gy.

In the present invention, the term "cytokine" refers to an immune activating cytokine that can be used to induce the NK cells from peripheral blood mononuclear cells. According to one exemplary embodiment of the present invention, IL-2, IL-15, IL-21, Flt3-L, SCF, IL-7, IL-12, or IL18 may be used as such a cytokine alone or in combination. In particular, since IL-2, IL-15 or IL-21 is known as a cytokine having an excellent effect in differentiation of the peripheral blood mononuclear cells into the NK cells and proliferation of the NK cells, it is desirable to use these cytokines. According to one exemplary embodiment of the present invention, IL-2 is used, but the present invention is not limited thereto.

The fact that the cytokines are associated with inducement into the NK cells may be found in various documents. From the fact that B cells and T cells are found in mice in which expression of γc of a cytokine receptor does not occur, and NK cells are not found in the mice, cytokine receptors containing γc are known to play an important role in differentiation into the NK cells (Singer, B et al., Proc. Natl. Acad. Sci. USA 92, 377-381, 1995). The γc type of the receptor includes receptors of IL-2, IL-4, IL-7, IL-9, IL-15, and IL-21. Among these, IL-2 is reported to have a function which promotes proliferation and activation of mature NK cells (Shibuya, A. et al., Blood 85, 3538-3546, 1995). It has been reported that the number of the NK cells is significantly lowered in humans and mice which lack IL-2 (DiSanto, J. P. et al., J. Exp. Med. 171, 1697-1704, 1990). On the other hand, there are studies showing that the lack of IL-2 and IL-2Ra indirectly exert an influence on the number and activation of the NK cells. In addition, an IL-2R chain is known to play a part in formation of an IL-15 receptor.

The IL-15 plays a part in differentiation into NK cells. This is found from the fact that the NK cells are lacking in the mice which lack transcription factor interferon (IFN)-regulatory factor 1 required for IL-15 production (Kouetsu et al., Nature 391,700-703, 1998), and that the NK cells are not found in the mice in which IL-15 or IL-15Ra is lacking. As a result, it has been reported that IL-15 directly promotes growth and differentiation of the NK cells by means of the IL-15 receptor expressed in the NK cells (MrozekE et al., Blood 87, 2632-2640, 1996).

IL-21 is a cytokine secreted by activated CD4+ T cells (Nature, 5:688-697, 2005), and the IL-21 receptor (IL-21R)

is expressed in lymphocytes such as dendritic cells, NK cells, T cells, and B cells (Rayna Takaki, et al., J. Immonol 175: 2167-2173, 2005). IL-21 is structurally highly similar to IL-2 and IL-15, and IL-21R shares a chain with IL-2R, IL-15, IL-7R, and IL-4R (Asao et al., J. Immunol, 167: 1-5, 2001). IL-21 has been reported to induce maturation of an NK cell precursor from bone marrow (Parrish-Novak, et al., Nature, 408: 57-63, 2000), particularly promote effector functions such as an ability of the NK cells to produce cytokines and kill cells (M. Strengell, et al., J Immunol, 170, 5464-5469, 2003; J. Brady, et al., J Immunol, 172, 2048-2058, 2004), and promote the anti-cancer response of the innate and adaptive immune systems by enhancing the effector functions of CD8+ T cells (Rayna Takaki, et al., J Immunol 175, 2167-2173, 2005; A. Moroz, et al., J Immunol, 173, 900-909, 2004). Also, IL-21 has been reported to activate the NK cells separated from human peripheral blood (Parrish-Novak, et al., Nature, 408, 57, 2000), and induce mature NK cells from haematopoietic stem cells separated from cord blood (J. Brady, et al., J Immunol, 172, 2048, 2004).

According to one exemplary embodiment of the present invention, cytokine may be used at a concentration of 50 U/ml to 1,000 U/ml, for example, 200 U/ml to 800 U/ml, or 400 U/ml to 600 U/ml. A conventional method of expanding NK cells requires a high concentration of various cytokines, but in the method of expanding NK cells according to one exemplary embodiment of the present invention, the NK cells may be proliferated with high yield and purity even when one cytokine is used at a low concentration due to the use of two types of feeder cells.

In the present invention, a typical medium may be used without limitation as long as a medium that may be used in the culture of the peripheral blood mononuclear cells can be used to induce the peripheral blood mononuclear cells to become NK cells and proliferate the NK cells. For example, an RPMI, DMEM, x-vivo10, x-vivo20, or cellgro SCGM medium may be used as such a medium. In addition, the culture conditions such as temperature and the like may correspond to the typical culture conditions for the peripheral blood mononuclear cells.

According to one exemplary embodiment of the present invention, the peripheral blood mononuclear cells, the irradiated Jurkat cells and the irradiated EBV-LCL cells may be co-cultured for 7 days to 30 days, for example, 10 days to 20 days. Preferably, the co-culturing is efficiently performed for 10 days to 14 days.

According to another exemplary embodiment of the present invention, when the peripheral blood mononuclear cells are co-cultured with the feeder cells, the peripheral blood mononuclear cells and the feeder cells may be mixed at a mixing ratio of 1:5 to 2:1.

According to one exemplary embodiment of the present invention, to determine an effect of the Jurkat cells and EBV-LCL cells as the feeder cells on inducement and proliferation of the NK cells, four different groups are cultured for a predetermined period of time as follows: a group in which the mononuclear cells are cultured in the presence of IL-2 (control 1), a group in which the mononuclear cells are cultured with the irradiated Jurkat cells in the presence of IL-2 (control 2), a group in which the mononuclear cells are cultured with the irradiated EBV-LCL cell in the presence of IL-2 (control 3), and a group in which the mononuclear cells are co-cultured with the irradiated Jurkat cells and the irradiated EBV-LCL cells in the presence of IL-2 as an experimental group. And, the PBMC and NK cells are then counted (see Example 2, and FIGS. 2 and 3).

Figure 2:
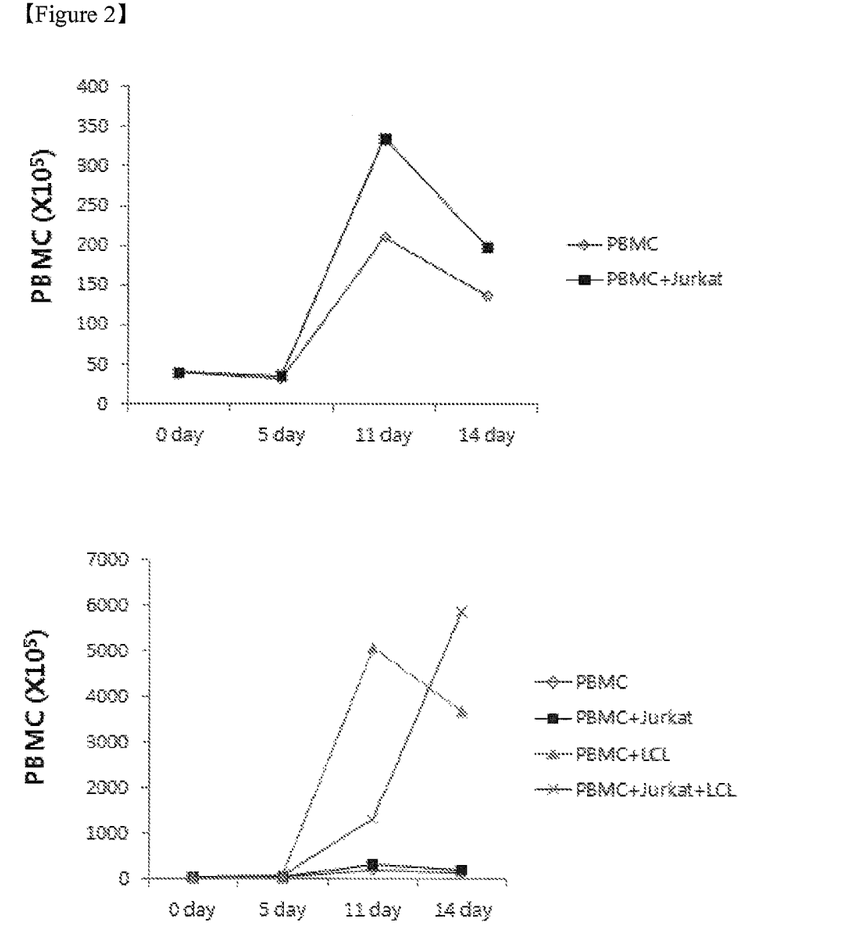
FIG. 2 is a graph plotted by measuring the number of the peripheral blood mononuclear cells (PBMCs) in a group in which PBMCs separated from a human are treated with only IL-2 (◇, PBMC), a group in which PBMCs are co-cultured with an irradiated Jurkat cell line in the presence of IL-2 (■, PBMC+Jurkat), a group in which PBMCs are co-cultured with an irradiated EBV-LCL cell line in the presence of IL-2 (▲, PBMC+LCL), and a group in which PBMCs are co-cultured with the irradiated Jurkat cell line and the irradiated EBV-LCL cell line in the presence of IL-2 (x, PBMC+Jurkat+LCL).
Figure 3:
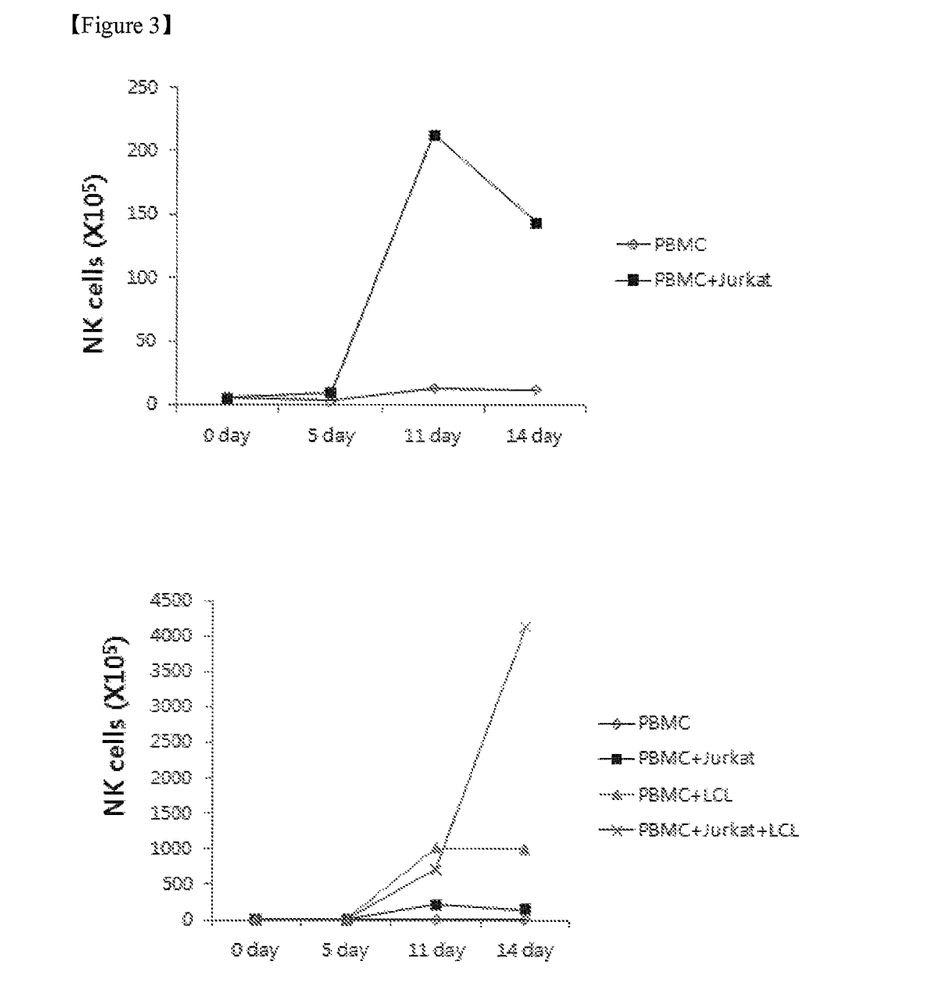
FIG. 3 is a graph plotted by measuring the number of the NK cells in the group in which PBMCs are treated with only IL-2 (◇, PBMC), the group in which PBMCs are co-cultured with an irradiated Jurkat cell line in the presence of IL-2 (■, PBMC+Jurkat), the group in which PBMCs are co-cultured with an irradiated EBV-LCL cell line in the presence of IL-2 (▼, PBMC+LCL), and the group in which PBMCs are co-cultured with the irradiated Jurkat cell line and the irradiated EBV-LCL cell line in the presence of IL-2 (x, PBMC+Jurkat+LCL).
Figure 4A:
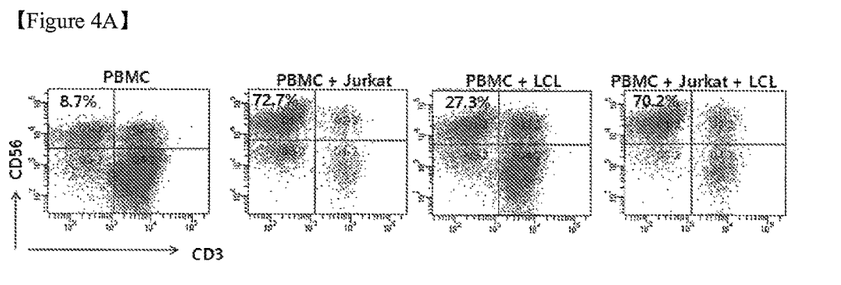
FIG. 4A shows the results obtained by analyzing enrichment levels of the NK cells using a flow cytometer in the group in which PBMCs are treated with only IL-2 (PBMC), the group in which PBMCs are co-cultured with an irradiated Jurkat cell line in the presence of IL-2 (PBMC+Jurkat), the group in which PBMCs are co-cultured with an irradiated EBV-LCL cell line in the presence of IL-2 (PBMC+LCL), and the group in which PBMCs are co-cultured with the irradiated Jurkat cell line and the irradiated EBV-LCL cell line in the presence of IL-2 (PBMC+Jurkat+LCL).

As a result, it is confirmed that the number of the PBMC increase approximately 147 times more in the experimental group in which the mononuclear cells are co-cultured with the irradiated Jurkat cells and the irradiated EBV-LCL cells in the presence of IL-2 than that in the controls (FIG. 2). In addition to the proliferation of the NK cells, a level of enrichment of the NK cells is also determined. As a result, it is revealed that the ratio of NK cell phenotypes, CD56+ and CD3 cells, increases to 70% or more in the experimental group in which the mononuclear cells are co-cultured with the Jurkat cells and the EBV-LCL cells in the presence of IL-2 after the 14-day culture (FIG. 4A).

Meanwhile, the method of expanding NK cells according to one exemplary embodiment of the present invention may further comprise adding the irradiated Jurkat cells, the irradiated EBV-LCL cells and the cytokines on day 1 to day 15 of a subsequent culture performed to maintain the NK cells after the inducement and proliferation of the NK cells derived from the peripheral blood mononuclear cells. The activated NK cells have a problem in that it is difficult to undergo immunotherapy using the activated NK cells due to their short lifetime. Therefore, the lifetime of the activated NK cells may be extended, and a larger amount of the NK cells may be obtained by adding the irradiated Jurkat cells, the irradiated EBV-LCL and the cytokines on day 1 to day 15 of the culture after the proliferation of the NK cells according to one exemplary embodiment of the present invention.

According to another aspect of the present invention, a composition for preventing and treating cancer including the NK cells derived from the peripheral blood mononuclear cells obtained by the above method, use of the NK cells derived from the peripheral blood mononuclear cells obtained by the method for preparing a medicament for prevention and treatment of cancer, or a method of preventing and treating cancer including administering an effective amount of the NK cells derived from the peripheral blood mononuclear cells obtained by the above method is provided.

According to one exemplary embodiment of the present invention, the NK cells obtained from the group in which the mononuclear cells are co-cultured with the irradiated Jurkat cells in the presence of IL-2 (control 2), the group in which the mononuclear cells are co-cultured with the irradiated EBV-LCL cells in the presence of IL-2 (control 3), and the group in which the mononuclear cells are co-cultured with the irradiated Jurkat cells and the irradiated EBV-LCL cells in the presence of IL-2 (an experimental group) are evaluated for their ability to kill cancer cells. As a result, it is revealed that the NK cells of the experimental group which proliferate approximately 800 higher than the controls have potency that kills cancer cells, which does not weaken.

Therefore, the NK cells obtained by the method according to one exemplary embodiment of the present invention may be effectively used to prevent and treat cancer.

According to one exemplary embodiment of the present invention, the subject may be a human in need of prevention and/or treatment of cancer. A subject may be a patient at risk of cancer, a normal person, or a cancer patient.

The composition for preventing and treating cancer comprising the NK cells derived from the peripheral blood mononuclear cells according to one exemplary embodiment of the present invention may be formulated into preparations in which the NK cells derived from the peripheral blood mononuclear cells are suspended at a proper concentration in an aqueous solution optionally including proper components (for example, a phosphate buffer, a typical aqueous solution for an injection, etc.)

The pharmaceutical composition for preventing and treating cancer according to one exemplary embodiment of the present invention may be administered via a typical route such as an intravenous, intraarterial, intraperitoneal, intramuscular, or intrasternal injection.

An effective amount of the NK cells derived from the peripheral blood mononuclear cells included in the pharmaceutical composition according to one exemplary embodiment of the present invention refers to an amount required to achieve an effect of preventing or treating cancer. Therefore, the effective amount of the NK cells may be adjusted according to the type of a disease, the severity of a disease, the types and contents of other components included in the composition, age, weight, general health conditions and gender of a patient, diet, an administration time, a route of administration, a treatment duration, and various factors including drugs used together with the NK cells. The NK cells derived from the peripheral blood mononuclear cells according to one exemplary embodiment of the present invention may, for example, be administered to an adult at a dose of $1\times10^6$ cells/kg to $1\times10^{11}$ cells/kg, for example, $1\times10^6$ cells/kg to $1\times10^8$ cells/kg, when administered once or in divided doses, but the present invention is not limited thereto.

Advantageous Effects

According to the present invention, a large quantity of the NK cells can be induced and proliferated from a small quantity of the peripheral blood mononuclear cells without using expensive equipment or various kinds of expensive cytokines, and thus the NK cells can be used to remarkably improve efficiency and efficacy in preventing and treating cancer.

BEST MODE

These and other advantages and features of the present invention and method of achieving them will be apparent from the following description of preferred embodiments, with reference to the accompanying drawings. However, the present invention is not limited to the following embodiments but will be embodied in various forms. That is, the embodiments of the present invention play a role of making the disclosure of the present invention complete, and are provided to inform a person who has an ordinary knowledge and skill in the art to which this invention belongs. This invention should be defined based on the scope of claims.

EXAMPLES

Example 1: Preparation of NK Cells from Peripheral Blood Mononuclear Cells

Human blood was collected and centrifuged at 2,500 rpm for 30 minutes in Ficoll (Ficoll-Paque™ PLUS, GE HealthCare), and peripheral blood mononuclear cells (PBMCs) were separated from a buffy coat. Thereafter, the PBMCs were stained with Tryphan Blue. Then, damaged cells were removed, and only unstained cells were counted using a hematocytometer.

A Jurkat cell line and an EBV-LCL cell line used as feeder cells were cultured at 37° C. in human RPMI media, which were obtained by adding 10% FBS and 1% penicillin/streptomycin to an RPMI1640 medium under a 5% $CO_2$ condition. A hRPMI medium supplemented with 500 U/ml of IL-2 was added once every 2 to 3 days, the cells were harvested at an interval of 5 days, and a fresh hRPMI medium supplemented with IL-2 was added.

Cell counts were measured using a hematocytometer, and the Jurkat cell line and the EBV-LCL cell line, both of which were present at a concentration of $1\times10^6$/ml, were irradiated with radiation of 100 Gy at an intensity of 2.22 Gy/min.

A hRPMI medium supplemented with 500 U/ml of IL-2 was put into wells of a 24-well plate, and the irradiated Jurkat cell line, the irradiated EBV-LCL cell line, and the previously separated mononuclear cells were cultured at a ratio of 1:0.5:0.5 and a temperature of 37° C. in an incubator into which 5% $CO_2$ was being supplied (an experimental group).

Also, a group in which the mononuclear cells were cultured in the presence of IL-2 in the same manner as described above without adding a feeder cell line (control 1), a group in which the mononuclear cells were cultured with irradiated Jurkat cells in the presence of IL-2 (control 2), and a group in which the mononuclear cells were cultured with irradiated EBV-LCL cells in the presence of IL-2 (control 3) were used as the controls.

Example 2: Measurement of Ability to Proliferate NK Cells

To determine an effect of the feeder cells on proliferation of the NK cells, the NK cells in the experimental group defined in Example 1, control 1, control 2, and control 3 were counted on 0 day, $5^{th}$ day, $11^{th}$ day, and $14^{th}$ day, and stained using antibodies against fluorescence-labeled CD56 and CD3. Thereafter, the NK cells were analyzed using flow cytometry to assay the groups of NK cells (CD56+, CD3−). Subsequently, the NK cells were counted using the sum of the enrichment levels of the PBMCs and NK cells.

As a result, it was revealed that the PBMCs increased approximately 147 times higher in the case of the experimental group (x, PBMC+Jurkat+LCL) in which both the Jurkat cells and the EBV-LCL cells were co-cultured with PBMCs than in the case of control 1 (◇, PBMC), control 2 (■, PBMC+Jurkat), or control 3 (▲, PBMC+LCL) on the $14^{th}$ day of culturing, as shown in FIG. 2. Also, it was revealed that the NK cells increased approximately 800 times higher in the experimental group than the controls on the $14^{th}$ day of culturing when both the Jurkat cells and the EBV-LCL cells were co-cultured with PBMCs.

Example 3: Measurement of Enrichment Level of NK Cells

Figure 4B:
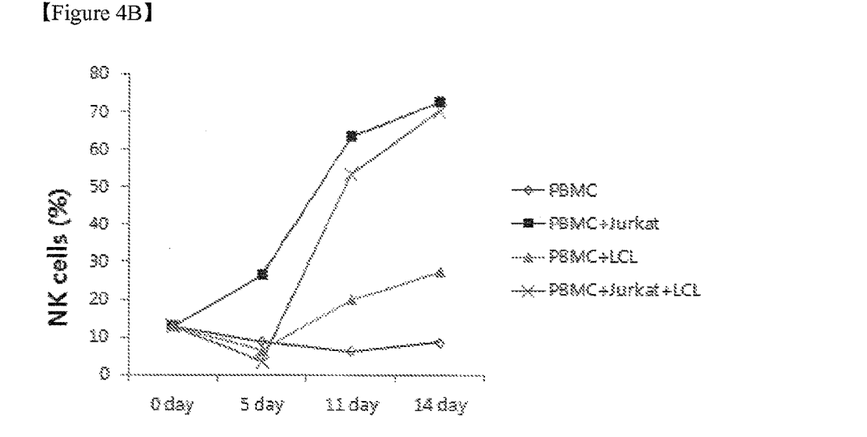
FIG. 4B is a graph illustrating the enrichment levels of the NK cells in the group in which PBMCs are treated with only IL-2 (◇, PBMC), the group in which PBMCs are co-cultured with an irradiated Jurkat cell line in the presence of IL-2 (■, PBMC+Jurkat), the group in which PBMCs are co-cultured with an irradiated EBV-LCL cell line in the presence of IL-2 (▲, PBMC+LCL), and the group in which PBMCs are co-cultured with the irradiated Jurkat cell line and the irradiated EBV-LCL cell line in the presence of IL-2 (x, PBMC+Jurkat+LCL).

To analyze an effect of the feeder cells and the cytokines on enrichment of the NK cells, the NK cells were stained using fluorescence-labeled CD56 and CD3 antibodies on 0 day, $5^{th}$ day, $11^{th}$ day, and $14^{th}$ day of culturing, and analyzed for the experimental group of Example 1, control 1, control 2, and control 3 using flow cytometry. As a result, it was revealed that the percentage of the NK cell phenotypes, CD56+ and CD3 cells, increased to 70% or more when the mononuclear cells were co-cultured with the Jurkat cells and the EBV-LCL cells after the 14-day culture (FIG. 4A). FIG. 4B is a graph illustrating the enrichment levels of the NK cells, as measured on the $14^{th}$ day of culturing using flow cytometry.

Example 4: Measurement of Ability of NK Cells Prepared According to One Exemplary Embodiment of the Present Invention to Kill Cancer Cells To evaluate an ability of the NK cells, which were prepared using the irradiated Jurkat cell line and irradiated EBV-LCL cell line of Example 1 as the feeder cells, to kill cancer cells, a $^{51}Cr$ release assay was performed using tumor cells (K562, Jurkat) as target cells.

First, the cancer cells K562 and the Jurkat cells were counted, and labeled with an isotope, $^{51}Cr$, and then reacted for an hour in a cell incubator. The isotope-labeled cancer cells were washed three times with a hRPMI medium to remove the isotope. The cells obtained in the experimental group of Example 1, control 2, and control 3 were counted using a hematocytometer, and then co-cultured with the isotope-labeled cancer cells at a ratio of 10:1, 3:1, or 1:1 for 4 hours. After 4 hours, the cells were centrifuged at 2,500 rpm for 5 minutes, and the supernatant was put into a tube and measured using a gamma counter.

Figure 5:
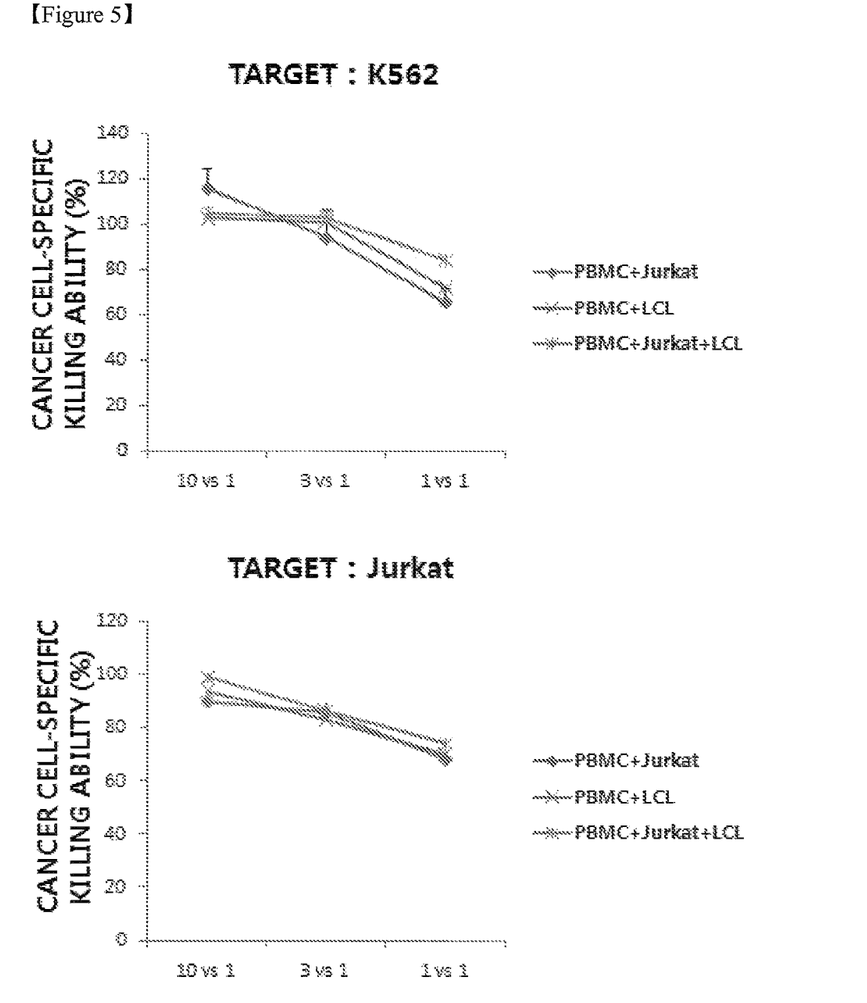
FIG. 5 is a graph plotted by evaluating the abilities of the NK cells to kill cancer cells in a group in which PBMCs are co-cultured with an irradiated Jurkat cell line in the presence of IL-2 (♦), a group in which PBMCs are co-cultured with an irradiated EBV-LCL cell line in the presence of IL-2 (x), and a group (*) in which PBMCs are co-cultured with both the irradiated Jurkat cell line and the EBV-LCL cell line, in the presence of IL-2.

As shown in FIG. 5, it could be seen that the ability of the NK cells to kill cancer cells was observed to be similar to that of control 2 (♦) in which the IL-2 and irradiated Jurkat cell line were used, in the case of the control 3 (x) in which the IL-2 and irradiated EBV-LCL cell line were used, and experimental group (*) in which both the irradiated Jurkat cell line and EBV-LCL cell line were co-cultured. Also, it was confirmed that the NK cells had a significant ability to kill cancer cells even when the effector cells and the target cells were present at an E:T ratio of 1:1.

As seen from these results, it could be seen that the peripheral blood mononuclear cells according to one exemplary embodiment of the present invention which were treated with the IL-2, the irradiated Jurkat cells, and the irradiated EBV-LCL cell, were enriched to become the NK cells and also had a superior ability to kill cancer cells.

Example 5: Measurement of Activation of NK Cells Prepared According to One Exemplary Embodiment of the Present Invention Example 4 showed that the NK cells, which were prepared using the irradiated Jurkat cell line and the irradiated EBV-LCL cell line prepared in Example 1 as the feeder cells, had a high ability to kill cancer cells. Thus, evaluating the presence of activation markers, expression of various NK cell-related activation and inhibitory receptors in the NK cells, which were cultured for 11 days, was examined using flow cytometry.

Figure 6:
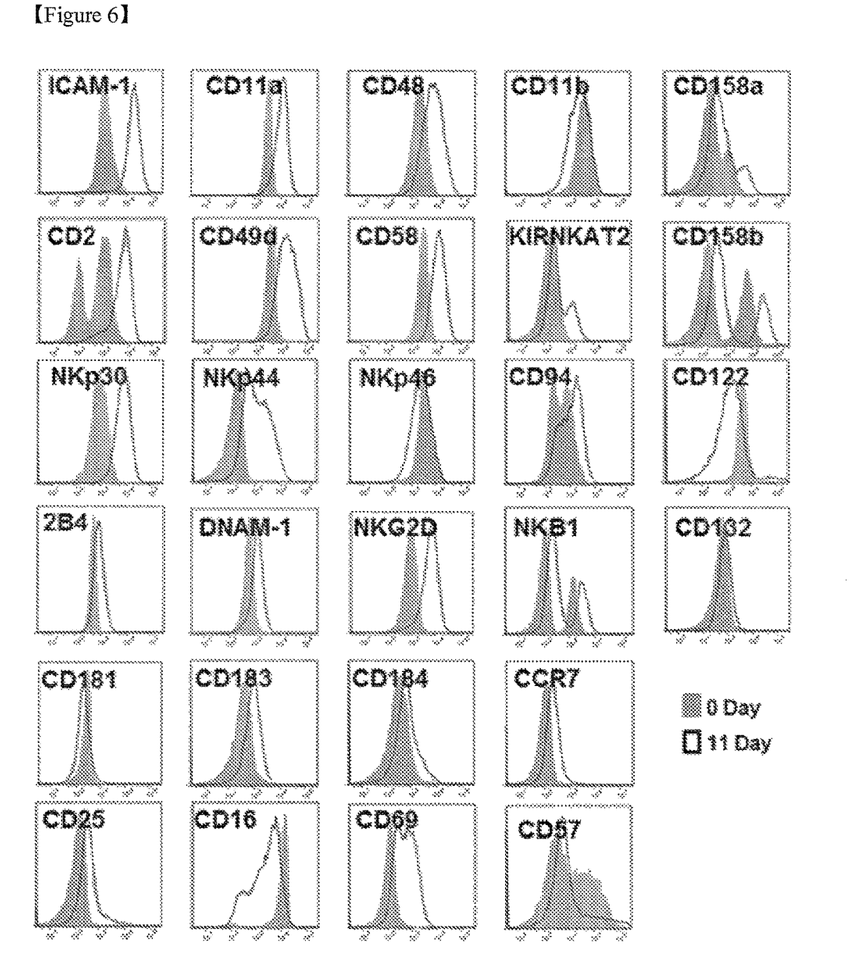
FIG. 6 shows the results obtained by analyzing activation of the NK cells prepared according to one exemplary embodiment of the present invention.

As shown in FIG. 6, it could be seen that the cell adhesion molecules such as ICAM-1, CD11a, CD48, CD2, CD49d, and CD58, the activation receptors such as NKp30, NKp44, 2B4, DNAM-1, and NKG2D, and the activation markers such as CD69, and CD25 were expressed at an increased level; the chemokine receptors such as CD183, CD184, and CCR7 were expressed at a slightly increased level; and the inhibitory receptors such as CD158a, CD158b, CD94, NKB1, and KIRNKAT2 were expressed at an increased level.

The invention claimed is:

1. A method for inducing and expanding natural killer (NK) cells derived from peripheral blood mononuclear cells, wherein the method comprises co-culturing irradiated Jurkat cells and irradiated Epstein-Barr virus transformed lymphocyte continuous line (EBV-LCL) cells as feeder cells with peripheral blood mononuclear cells in the presence of cytokines.

2. The method of claim 1, wherein the peripheral blood mononuclear cells are obtained from a normal person or a cancer patient.

3. The method of claim 1, wherein each of the irradiated Jurkat cells or the irradiated EBV-LCL cells is obtained by treatment with radiation of 100 to 500 Gy.

4. The method of claim 1, wherein the cytokines are one or more selected from the group consisting of IL-2, IL-15, IL-21, Flt3-L, SCF, IL-7, IL-12, and IL18.

5. The method of claim 1, wherein the method further comprises performing a subsequent culture to maintain the NK cells after inducement and proliferation of the NK cells derived from the peripheral blood mononuclear cells, wherein irradiated Jurkat cells, irradiated EBV-LCL cells and cytokines are added to the subsequent culture on the $1^{st}$ to the $15^{th}$ day of the subsequent culture.

* * * * *